United States Patent [19]

Fleisher et al.

[11] Patent Number: 5,440,053
[45] Date of Patent: Aug. 8, 1995

[54] RECOVERY OF MALTOL THROUGH AQUEOUS EXTRACTION

[75] Inventors: Alexander Fleisher, Wayne; Yan Gorenshteyn, Edgewater; Ilya Nakhimovich, Bloomfield; Olga Vselyubsvaya, Leonia, all of N.J.

[73] Assignee: Florasynth, Inc., Teterboro, N.J.

[21] Appl. No.: 240,112

[22] Filed: May 9, 1994

[51] Int. Cl.⁶ ............................. C07D 309/40
[52] U.S. Cl. .................................... 549/418
[58] Field of Search ........................ 549/418

[56] References Cited

U.S. PATENT DOCUMENTS 3,501,501 3/1970 Heintz et al.
5,221,756 6/1993 Fleisher et al.

OTHER PUBLICATIONS

Fleisher and Fleisher (1991) "Water-Soluble Fractions of the Essential Oils", *Perfumer and Flavorist* 16:37-41.
Goos and Reiter (1946) "New Products from Wood Carbonization", *Industrial and Engineering Chemistry* 38(2):132-135.
LeBlanc and Akers (1989) "Maltol and Ethyl Maltol: From the Larch Tree to Successful Food Additive", *Food Technology*, pp. 78-84.
Fleisher, A. (1990) "The Poroplast Extraction Technique in the Flavor and Fragrance Industry", *Perfumer and Flavorist* 15(5):27-36.

*Primary Examiner*—Nicky Chan
*Attorney, Agent, or Firm*—Scully, Scott, Murphy & Presser

[57] ABSTRACT

Disclosed is a process for recovering maltol from water-insoluble source material containing maltol, comprising extracting the maltol with a hot aqueous solution containing a solute which increases the immiscibility between said source material and said solution.

8 Claims, 1 Drawing Sheet

RECOVERY OF MALTOL THROUGH AQUEOUS EXTRACTION

FIELD OF THE INVENTION

This invention is related to a process for obtaining maltol.

Maltol (2-methyl-3-hydroxy-4-pyrone) is a heterocyclic aroma chemical used extensively in flavor and fragrance compositions. It is naturally occurring in numerous plant species, especially in coniferous trees such as Larix and Abias spp.

The presence of maltol in various plant sources has been known for many years and considerable efforts have been made to develop a sensible method for its commercial recovery. The existing techniques are, however, rather complex and the use of the resulting maltol is cost-prohibitive.

The solubility of maltol in ethylene glycol at ambient temperatures exceeds 4%. This completely prohibits economical maltol recovery from dilute mixtures, effectively eliminating virtually all natural sources. Moreover, there is a limiting practical consideration being that the crystallization of maltol from ethylene glycol at ambient temperatures is very slow. At very low temperatures the viscosity of ethylene glycol also considerably hampers filtration of maltol from ethylene glycol/maltol mixtures.

Ethylene glycol derived maltol is also unsuitable for food application, since the removal of toxic ethylene glycol contamination from maltol is rather difficult.

Maltol can be obtained in very small amounts from the destructive distillation products of wood, and by a partially synthetic process from kojic acid, which is obtained from fermentation media. However, maltol, obtained therefrom, is still quite expensive.

Maltol has been reported to be in the bark of some species of larch trees. Maltol is present in larch bark in combined form to an extent varying from about 0.1 percent to about 2 percent by weight depending upon the bark layer and the season of harvest. The richest supply of maltol is found in the bark of roots of the larch trees although, for practical reasons, not much root bark is harvested. Large quantities of larch trees and bark containing maltol exist and are available primarily in the northwest part of the United States and southwest Canada. The bark is available at sawmills where it is stripped off of larch trees and stored in a pile, there to be burned for fuel or otherwise used if economical processes for recovering useful components therefrom can be found.

It is also known that maltol is present in various parts of coniferous species and found in rather large concentrations in the oleoresin extracted from fresh foliage of balsam fir (Abias balsamea L.).

U.S. Pat. No. 5,221,756 discloses that sufficiently pure maltol can be effectively recovered from the said resin through the co-distillation with a suitable hydrocarbon and, in particular, alpha-pinene. The process of co-distillation, although effective, requires a rather complex technological set-up, application of vacuum, high pressure steam and necessary handling of flammable liquids. During co-distillation maltol crystallizes directly from the gaseous phase in a microcrystalline form. Thus maltol obtained from the co-distillation process retains substantial quantities (30 to 40%) of the hydrocarbon which complicates further purification.

On the other hand, fir balsam resin is a valuable product for the perfume industry for its fine and delicate organoleptic qualities. During co-distillation this material can suffer from long exposure to high temperatures which alters the organoleptic profile of the resin and consequently reduces its value as an aroma ingredient.

Alternative methods for the recovery of maltol especially adapted to its separation from oleoresin of coniferous species, suffer from various practical shortcomings.

Oleoresin with high maltol content can only be recovered from fresh fir foliage through extraction by a relatively polar water-immiscible solvent. This is due to the fact that maltol is insoluble in hydrocarbons, which eliminates all this class from the list of potential extractants. On the other hand, application of water miscible solvents such as alcohol and acetone is also excluded since such solvents will dissolve all the water contained in the fresh plant material. This results in an extracted product in which the water content can reach 50-60%, leading to undesired difficulties in recovering the maltol from the blend of solvent and water. Processes in which the extractant is limited to water-immiscible solvents for the oleoresin result in obtaining water insoluble oleoresin that contains maltol.

It is known that maltol is substantially soluble in hot water (about 20% at boiling) while its solubility at low temperatures is reduced (about 0.7% at 0° C). However, it is possible to extract maltol from fir oleoresin by pure hot water and subsequently to recover maltol from the aqueous solution. Such an extraction needs to be conducted at elevated temperature since at room conditions the resin is extremely viscous. Unfortunately, the specific gravity of the resin is very close to that of water. Intensive mixing of hot water and resin results, therefore, in formation of a stable emulsion which makes the separation of the liquid phases rather difficult.

Thus, there remains a need for an efficient, practical process for recovering maltol from source material, particularly where the source material is oleoresin.

BRIEF SUMMARY OF THE INVENTION

According to the present invention, maltol is recovered from source material, particularly water insoluble source material, and especially from oleoresin of coniferous species. In particular, maltol is recovered from fir balsam resin. The source material is extracted with a hot aqueous salt solution, and specifically, a hot, aqueous solution of sodium chloride. This is followed by the recovery of maltol from the aqueous solution and, in particular, by direct crystallization of maltol from said aqueous phase.

BRIEF DESCRIPTION OF THE DRAWINGS

The Figure is a flowsheet of an extractive process useful in the present invention.

DETAILED DESCRIPTION OF THE INVENTION

Figure 1:
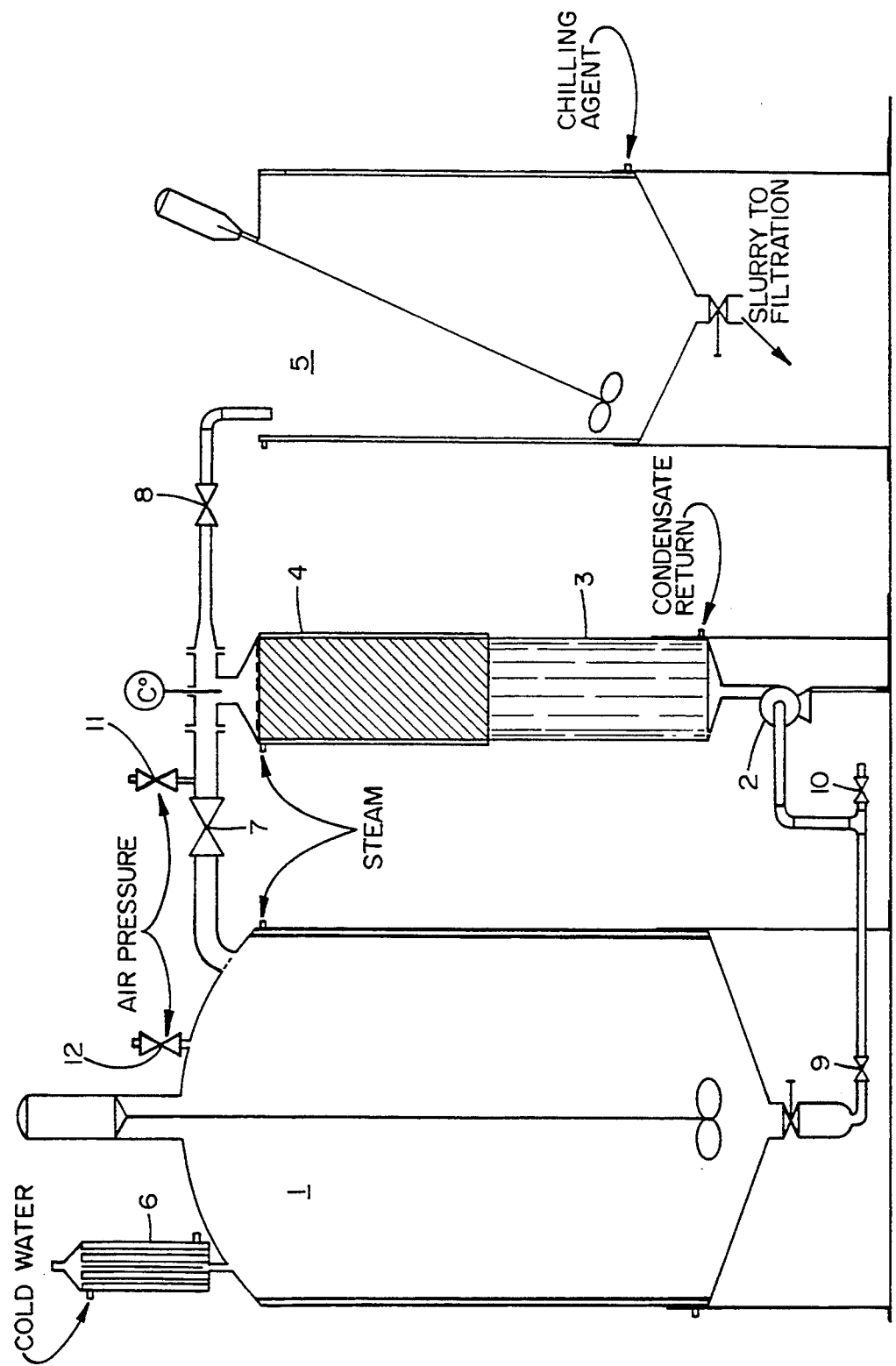

Source material that can be treated in the process of the present invention includes virtually any maltol-containing matter that contains water-insoluble components. Preferred source material includes oleoresinous fractions that can be obtained by prior treatment of plant material, such as plant matter from balsam fir, larch, or other coniferous plant matter. An example of a particularly preferred source material is oleoresin, such as balsam fir resin.

The source material can contain water, but the water content is preferably low, e.g., up to about a few weight percent.

The source material is extracted with an aqueous solution. The solution contains dissolved therein one (or more) solutes which acts to increase the specific gravity of the water, and has (or have) the property that it (or they) increase the immiscibility between the water-soluble material and the aqueous phase. Immiscibility can be increased in the sense of reducing the solubility of the source material other than maltol in the aqueous phase, by reducing the solubility of the aqueous phase in the source material, and/or by reducing the tendency of the two phases to form a third phase or stable emulsion. Immiscibility can also be increased in the sense of decreasing the settling time, that is, the time required for a mixture of the source material and the aqueous phase to form two distinct, cleanly defined layers.

The solute material also needs to have the property that at low temperature, i.e., at a temperature in the range of 0° C. to 20° C., it is more soluble in water than the maltol is. Preferably, the solute material is dissolvable from the recovered maltol; and it is preferred that the solute material be compatible with uses for the maltol that require contact with the human body, including ingestion by humans.

Suitable solute materials include nonionic and ionic compounds. Exemplary of nonionic materials are sugars and sugar alcohols such as dextrose, glucose, sucrose, fructose, mannitol and sorbitol. More complex carbohydrates and polysaccharides are included as well. Other nonionic materials include lower alkanols containing up to 6 carbon atoms, glycols containing up to 6 carbon atoms, such as propylene glycol, diethylene glycol, and water-soluble longer chain poly(alkoxy) compounds wherein each alkoxy unit is ethoxy or propoxy.

Preferably, the solute materials should not act as surfactants which would lessen the immiscibility of the source material and the aqueous phase.

Other suitable solute materials are ionic compounds, that is, salts.

The salt is preferably sodium chloride, for reasons of effectiveness as well as economy. Other water-soluble inorganic and organic salts can also be employed, notably any water-soluble halide (e.g., fluoride, chloride, bromide, iodide) salts of alkali metals and water-soluble halide salts of calcium, magnesium or other alkaline earth metals. Other useful anionic groups include carbonates, bicarbonates, nitrates, sulfites, sulfates, phosphates, and organic anions preferably including alkanoates containing up to 6 carbon atoms, such as acetate and propionate, and polybasic organic anions such as citrate. Terms such as "sulfate" and "phosphate" are intended to include any analogs having a valence from $-1$ to the maximum; thus analogs such as $HSO_4^-$ and $H_2PO_4^-$ are intended to be included. Other useful cationic groups include ammonium and metals such as aluminum, manganese, iron, cobalt, nickel, copper and zinc. Mixtures of two or more salts can also be used.

The concentration of the solute material in the solution will depend somewhat on the identity of the source material and the identity of the solute material being used. Generally, solutions containing about 1 wt.% to about 20 wt.% are useful. Solute concentrations of 1 wt.% to 10 wt.% are preferred, and especially concentrations of about 4 wt.% to about 7.5 wt.%.

The amount of solute present should be sufficient to increase the specific gravity of the aqueous phase enough to improve the ease of separating the phases. Too low a solute content is undesirable because subsequent separation of the aqueous and resinous phases is difficult. Too high a solute content is undesirable because it would lessen the solubility of the maltol in the aqueous phase.

When sodium chloride is being used, amounts of about 5 to about 10 wt.% are useful, generally about 5 to about 7.5 wt.%.

The solution with the solute material is contacted together with the source material in a vessel, such as an agitated tank, in a manner to provide close contact between the solution and the source material. Contact is preferably increased by thoroughly mixing the materials together. The ratio of solution to source material is generally about 100:1 to about 1:100. It is a straightforward matter to determine the optimum ratios for any given source material and conditions. The ratio will of course depend on the solute content of the solution.

The solution as it contacts the source material is preferably at elevated temperature. While temperatures above about 20° C. are useful, temperatures of at least 50° C. or even at least 80° C. to 100° C. are more useful as greater amounts of maltol can be extracted.

The solution and the source material are preferably maintained in close contact for a length of time (up to several hours) sufficient to reach equilibrium of maltol between the source material and the solution.

Following the contact, the solution and the source material are allowed to settle, the aqueous solution is separated, and preferably filtered. The solution can then be treated to recover the maltol therefrom. For instance, the solution can be cooled (preferably to near 0° C.) so as to crystallize solid, crude maltol. The maltol can be recovered, washed, or otherwise further purified as necessary and used as a flavoring agent and/or an aroma agent. This aspect of the process takes advantage of the higher low-temperature solubility of the solute material.

The process of the present invention has several advantages. In particular, it affords improved yields of maltol compared to extractive processes not using an aqueous solution as described herein. The solution is also believed to have improved selectivity in that it solubilizes the maltol yet solubilizes less of other co-products present in the source material. This feature eases the subsequent purification of the maltol following recovery thereof from the solution. Also, this process does not introduce reagents that could contaminate the maltol or cause it to be unacceptable for use in food or personal care products. It also does not create an environmental hazard. Such solute that remains in the product is easily washed out of it. The process also does not expose the maltol to conditions which could adversely affect the maltol itself, as by thermal or chemical decomposition or otherwise. If fir balsam is used as source material, it retains its organoleptic properties.

The invention is further described in the following examples:

EXAMPLE 1

973.6 grams of resin which contained 8.92% maltol was loaded into a cylindrical jacketed steam heated glass separatory vessel. The resin was sequentially extracted using a mechanical stirrer with two portions of 7% sodium chloride solution in water. The volume of the aqueous phase was two liters each time. The temperature of the resulting extraction mixture was maintained at 90° C. and the mixing time was three hours for each extraction stage.

After each stage, the phases were allowed to separate. The hot aqueous portions were drained, filtered and placed into a refrigerator to crystallize out maltol. Precipitated crystals of maltol were filtered out at 4° C. 48.4 grams of crude maltol were recovered which still contained about 15% of moisture. The residual concentration of the maltol in the resin after the two aqueous extraction stages was found to be 1.86% which corresponds to recovery of 80.6%. The residual maltol content in the mother-liquor was found to be 0.7%.

The recovered maltol was a reddish macro crystalline mass. This material was re-crystallized twice from 90% aqueous methanol in the presence of 1000 ppm of EDTA (ethylene diamine tetraacetic acid) resulting in snow white flavor grade maltol.

Simple mechanical agitation of resin in an aqueous salt solution, such as carried out in accordance with Example 1 above, can require a substantial time for equilibrium to be reached. In order to speed up the establishment of the equilibrium and increase the efficiency of maltol recovery by aqueous extraction, a special mixing/settling device was designed and constructed. It is schematically presented in the Figure and described as follows.

Both resin and aqueous phase are loaded into blending/settling tank (1) where the mixture is warmed up under stirring to about 100° C. Reflux condenser (6) prevents water and essential oil (naturally found as a component of the resin) from escaping the system. The hot blend of resin and aqueous phase is taken from the bottom of the tank by the pump (2) and transferred to a heat exchanger/static mixer (3), and then enters contactor (4) packed with sturdy high surface, low resistance Teflon-coated packing material. This material is well wetted by the resin which forms a thin layer moving on the surface of the packing material surrounded and tightly contacted by the aqueous phase. The emerging liquid is returned to the tank through the open valve (7). When equilibrium is established the valve (7) is closed and the mixture is pushed out from the contactor back into tank (1) by opening air pressure valve (11) and (12). All wetted parts were Teflon coated.

At this point valve (9) is closed. The tank mixer is stopped and the liquid phases are allowed to separate in the tank (1). The valve (9) is then opened, and the separated aqueous phase is pushed out through valve (9) by air pressure through valve (10); it passes through the contactor, which in this case acts as a filter and retains on its surface the micro-inclusions of the resin. Through open valve (8) the aqueous phase which contains maltol is dropped into chilled vessel (5), where maltol crystallizes out under slow mixing. Crude maltol is obtained from the resulting slurry by filtration.

EXAMPLE 2

185 kg of fir balsam resin which contained 5.0% maltol was loaded into tank (1) of the above-described system. 370 kg of 7% sodium chloride solution was added. This solution was used in a previous extraction and was already saturated with maltol at 3° C. This corresponds to 0.6% maltol in the aqueous phase. The mixture was warmed up to 95° C. At that point pump (2) was turned on and the mixture recirculated through the contactor for one hour. The system was stopped for a short time to take a sample of the aqueous phase. After that the recirculation continued for an additional two hours, whereupon it was stopped and a sample of the aqueous phase was again taken. The content of maltol in the aqueous phase after one hour of extraction was found to be identical to that taken after three hours. This means that the equilibrium was established in one hour or less.

The mixture was pushed out of the contactor into tank (1) and was allowed to settle for three and one-half hours. The aqueous phase thus formed was then transferred into chilled vessel (5) and allowed to cool down under stirring until the temperature reached 3° C.

The extraction was repeated under identical conditions. However, for the second time fresh 7% sodium chloride solution was used. The residual concentration of the maltol in the resin after two extractions was found to be 1.18% which corresponds to 77.3% recovery. 9.4 kg of crude wet maltol were recovered. The water content was found to be 24%.

The maltol content in the spent fir resin can be further reduced through additional extraction. Substantial quantities of maltol remain in the mother-liquor. This can be reduced either by decreasing the crystallization temperature, changing the concentration of the salt solution used for the extraction, vaporizing mother-liquor, or any other conventional method.

What is claimed is:

1. A process for recovering maltol from water-insoluble source material containing maltol, comprising:
   contacting said source material with a solution in water of solute material, wherein said solute material is an alkali or alkaline earth metal halide which increases the specific gravity of said water and which increases the immiscibility of said water with said source material, which alkali or alkaline earth metal halide is more soluble in water at low temperatures than said maltol, under conditions effective to extract maltol from said source material into said solution; and
   separating said maltol from said solution and said alkali or alkaline earth metal halide.

2. A process according to claim 1 wherein said maltol is separated from said solution by crystallizing said maltol from said aqueous solution.

3. A process according to claim 1 wherein said source material comprises oleoresin obtained from plant material.

4. A process according to claim 3 wherein said solute material is alkali metal halide.

5. A process according to claim 1 wherein said solute material is sodium chloride.

6. A process according to claim 4 wherein said alkali metal halide is sodium chloride.

7. A process according to claim 6 wherein said solution contains about 4 to about 10 wt.% sodium chloride dissolved therein.

8. A process according to claim 1 wherein said source material is contacted with said solution at a temperature greater than about 20° C.

* * * * *